United States Patent

Dowdy

[11] Patent Number: 5,975,082
[45] Date of Patent: Nov. 2, 1999

[54] TEAR-AWAY SURGICAL DRAPE

[75] Inventor: Richard C. Dowdy, Duluth, Ga.

[73] Assignee: Kimberly-Clark Worldwide, Inc., Neenah, Wis.

[21] Appl. No.: 08/901,568

[22] Filed: Jul. 28, 1997

Related U.S. Application Data

[63] Continuation of application No. 08/815,978, Mar. 10, 1997, abandoned.

[51] Int. Cl.$^6$ ................................................. A61B 19/00
[52] U.S. Cl. ................................................. 128/849; 128/853
[58] Field of Search ........................................ 128/849–856

Primary Examiner—Michael A. Brown
Attorney, Agent, or Firm—Dority & Manning, P.A.

[57] ABSTRACT

A tear-away surgical drape is provided by the present invention. The drape has a fluid absorbent pad attached to the upper surface of an underlying base sheet. The drape has an opening, or fenestration, therein through which the operation is to be performed. The absorbent pad has a score line in it which extends from an edge of the pad to the fenestration so that it, like the tear-away material forming the base sheet, may be easily torn away after surgery. The present drape is particularly useful when it is necessary to leave a tube, catheter, or other apparatus attached o the patient after the surgery. The tear-away aspects of the drape allow it to be removed without disturbing the attached apparatus.

11 Claims, 4 Drawing Sheets

TEAR-AWAY SURGICAL DRAPE

This is a continuation of application Ser. No. 08/815,978, filed Mar. 10, 1997, now abandoned.

FIELD OF THE INVENTION

The present invention relates generally to drapes for covering a patient's body when undergoing an operation or other medical procedure. More specifically, the present invention relates to tear-away surgical drapes having one or more fenestrations or openings therein through which a surgical procedure is to be performed.

BACKGROUND OF THE INVENTION

Drapes are used during surgical procedures, in part, to provide a sterile field about the surgical site and during other treatment procedures requiring the maintenance of a sterile environment. When used during surgery, drapes prevent blood and other bodily fluids from cross contaminating the sterile field since the reinforcement areas are usually absorbent. If designed correctly, the absorbent area of a surgical drape facilitates cleanup and movement of the patient after the operative procedure.

A variety of surgical drapes exist, but most share several common features. Surgical drapes will have one or more openings or apertures (more commonly known in the medical field as "fenestrations") through which the surgical procedure is performed. Most drapes are made of a water-repellent or water-impermeable material, or are coated with such a material, to prevent passage of bodily fluids as well as contaminating microorganisms. Many of today's surgical drapes are made of disposable nonwoven fabrics, plastic film, or papers.

An adhesive material is normally attached to the periphery of the drape material that defines the fenestration(s) so that the drape can be held in place around the surgical site and so that blood will not pass between the drape and the patient's body. The combination of the drape itself and the adhesive material around the perimeter of the aperture ensures a barrier between the surgical wound and the remainder of the body.

Currently, both disposable non-woven as well as reusable woven surgical drapes are used to create the sterile field for operative procedures. Some drapes employ a primary base sheet in conjunction with a smaller sheet, or pad, that is often made of an absorbent material backed by a liquid impervious film. When used, the reinforcing, absorbent pad is superimposed over the larger base sheet and is often connected thereto with an adhesive. Both the base sheet and the smaller pad have one or more corresponding apertures which define the surgical sites. An example of a surgical drape with a reinforcing, absorbent pad is shown in U.S. Pat. No. 3,902,484 to Winters.

Cardiac catheterization and angiography procedures are surgical procedures that, due to their nature, present special requirements for a surgical drape. Cardiac catheterization is the introduction of a catheter (a long slender tube) into the heart in order to obtain information about the structure and function of the heart, the cardiac valves, the coronary arteries, and the like. The catheter is typically introduced through an artery or vein.

Angiography is a procedure wherein a dye is injected into the blood vessels and then some type of medical photograph such as an x-ray is taken of the blood vessels containing the dye. The dye is introduced through a catheter at various points on the body, depending on the areas and organs being analyzed. This evaluation of the blood flow to and from organs can detect diseases that affect the blood vessels, such as aneurysms, atherosclerosis, and thrombosis. After the angiography procedure is completed, the patient will often be asked to remain lying flat in bed for anywhere from 6 to 8 hours.

One particular angiographical procedure is a percutaneous femoral angiography. During this diagnostic fluoroscopy procedure, a catheter probe is used to determine blockages to the heart. The catheter enters the body in the lower groin area near the femur and runs up the body in the direction of the heart. Obviously, in surgical drapes used for this procedure, one or more fenestrations are located on a sheet to correspond to the lower groin/upper femur area. During the procedure, one or both of the fenestrations (if two openings are present in the sheet) may be used for insertion of various apparatus. If two fenestrations are present, and only one is used during the operation, access to the other fenestration may be blocked by various sheets, etc. as is known in the art.

A surgical drape which is designed specifically for brachial angiography is described in U.S. Pat. No. 5,074,316 to Dowdy. As shown therein, a catheter is introduced through the brachial artery to determine the pressure within the heart, determine abnormalities in the structure of the heart, and the like. The direct brachial angiography approach uses a catheter inserted through the patient's arm which is then manipulated by the surgeon through the artery into the heart.

Many of these types of procedures require that elongated or enlarged apparatuses such as wires, catheters, intravenous supply tubes, intraaortic balloon pump connections, and the like, be placed into the patient at the surgical site. In many of these operations, such apparatuses remain in the patient for some time after the surgery is complete. For example, during a percutaneous transluminal coronary angioplasty, anticoagulants such as heparin, are often administered to patients to enable coronary dialysis. In addition to heparin, such patients may also receive drugs such as beta blockers that increase blood thinning. After completing this particular procedure, the surgical wound site must clot to promote healing. Typically, direct pressure is applied to the arterial site to promote the clotting. In some cases, there is a need to maintain an intraaortic balloon pump at the site to aid in coronary blood flow for a substantial period after the operation.

In cases where wires, tubes, blood pumps, and the like, remain in the patient after surgery, soiled surgical drapes must be removed from the patient. Because such apparatus is received into the body through the apertures in the base sheet/pad, it has been a problem to remove the drape after the procedure has been completed. Although the base sheet is often made of an easy to tear material, the stronger absorbent pad usually requires the use of scissors or other cutting instrument to remove it from the patient. Obviously, the use of scissors near the surgical site after closure is not preferred due to risk to the patient.

This problem has been addressed in the past by utilizing drapes having perforations which aid in the removal of the drape from the patient. A drape of this type is shown in the prior art FIGS. 1 and 2 of U.S. Pat. No. 5,109,873 to Marshall. These Figures do not show the use of a reinforcing pad as in the present invention and, therefore, do not address the problem of tearing away this stronger pad. In addition, although the perforations in this singular drape sheet create a weakened line on the drape so that it may be pulled apart by hand without the need for scissors, the presence of the perforations reduces the ability of the drape to form a sterile field which is impervious to liquid and microorganisms.

Marshall (U.S. Pat. No. 5,109,873) also shows a tear-away drape with a singular sheet having a "V"-shaped score line extending from an edge of the sheet to the opening. Like the prior art shown in FIGS. 1 and 2 therein, Marshall does not show the use of an absorbent or reinforcement pad superimposed over a base sheet to provide the benefits obtained by use of such a pad in the present invention. Likewise, Marshall does not address the problem created by removal of the pad from the patient. Moreover, as shown in FIG. 4, the score line does not pass all the way through the sheet but, instead, extends to a depth of between 35% to 50% of the total thickness of the drape.

Thus, there is still a need for further improved surgical drape designs having a base sheet and a pad which allow quick tear-away removal from sites where an apparatus must remain connected to the patient after an operation.. Such improved drapes should still preserve the desired sterile field around the site, but be constructed to allow quick and easy removal from the patient.

SUMMARY OF THE INVENTION

It is an object of the present invention to provide an improved surgical drape for use in surgical procedures such as those wherein a catheter, tube, or wire is inserted within a vein or artery of a patient and should remain inserted after completing the procedure.

Another object of the present invention is to provide a tear-away surgical drape for use in surgical procedures wherein the drape has one or more fenestrations through which the surgery is performed.

A further object of the present invention is to provide a tear-away surgical drape having a reinforcement pad for absorbing bodily fluids from around the surgical site.

These and other objects are achieved by providing a surgical drape having one or more tear-away aperture features that allow the drape to be removed from a patient without disturbing any catheters, pump lines, or other such intravenous apparatus which may still be in place in the patient's body. Specifically, the drape includes a base sheet defining one or more fenestrations at locations where surgical incisions will occur for the particular operation. An adhesive area surrounds the fenestration and is located on the side of the base sheet which will come into contact with the patient's body. When in place, this pressure-sensitive adhesive maintains the drape in place and forms a closed area between the patient's body and the base sheet to prevent fluids at the operative site from leaking underneath the drape.

A reinforcing, absorbent pad is superimposed on the upper surface of the base sheet. The pad has fenestrations through it which match the location of the fenestrations in the base sheet. The pad may be adhered to the base sheet and provides a fluid absorbing sheet for absorbing fluids near the operative site. The pad has a perforation score line running to the pad's aperture(s). Either one or both of the base sheet and the pad may have one or more notches at their edges which correspond in relative position to the score line on the pad.

After the surgical procedure is completed, the drape may be torn away without disturbing any apparatus still remaining connected to the patient at the surgical site. One merely begins tearing the base sheet at the notch (if present) on the edge, continues tearing the base sheet until the perforation score line on the pad is reached, and continues tearing both the base sheet and the pad until the tear goes to the fenestration. The base sheet and pad are then pulled back away from the patient and the drape may then be completely removed and disposed of without touching the remaining apparatus. Obviously, it is preferred that this invention utilize disposable materials.

In one embodiment of the present invention, the surgical drape is specifically designed for use during a femoral angiography procedure. The drape may be designed for use with any surgical procedure, such as, for example, cardiac catheterization and brachial angiography.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

Figure 1:
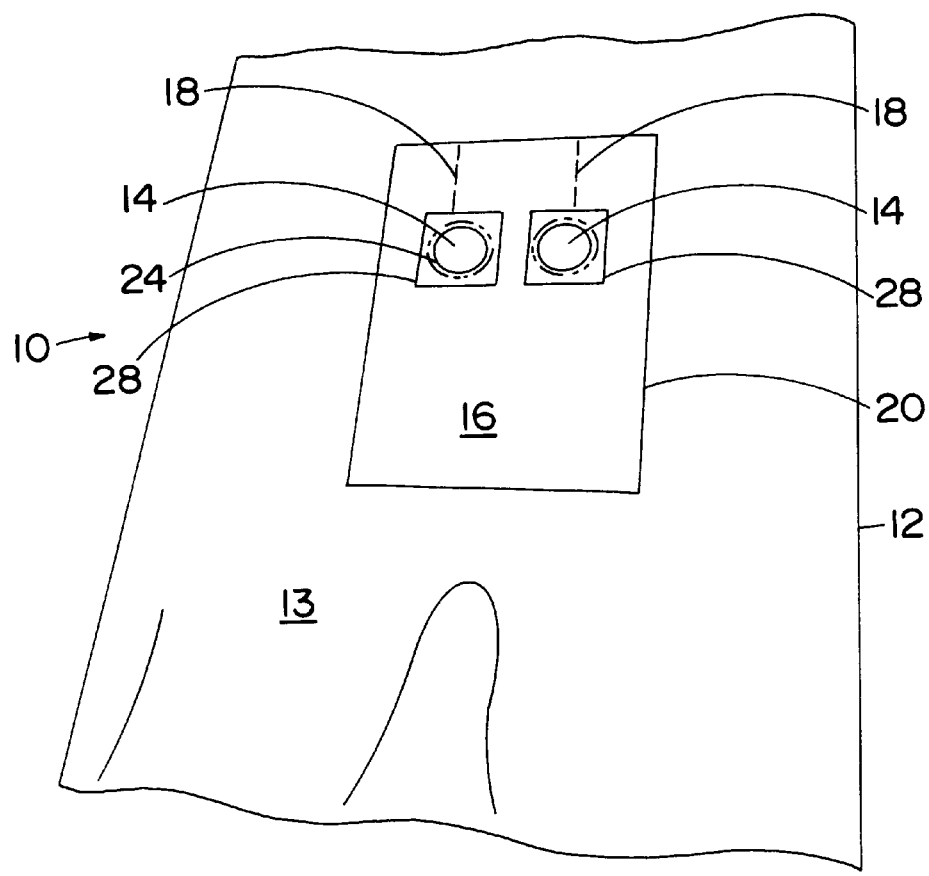
FIG. 1 is a plan view of a surgical drape in accordance with an embodiment of the present invention.
Figure 2:
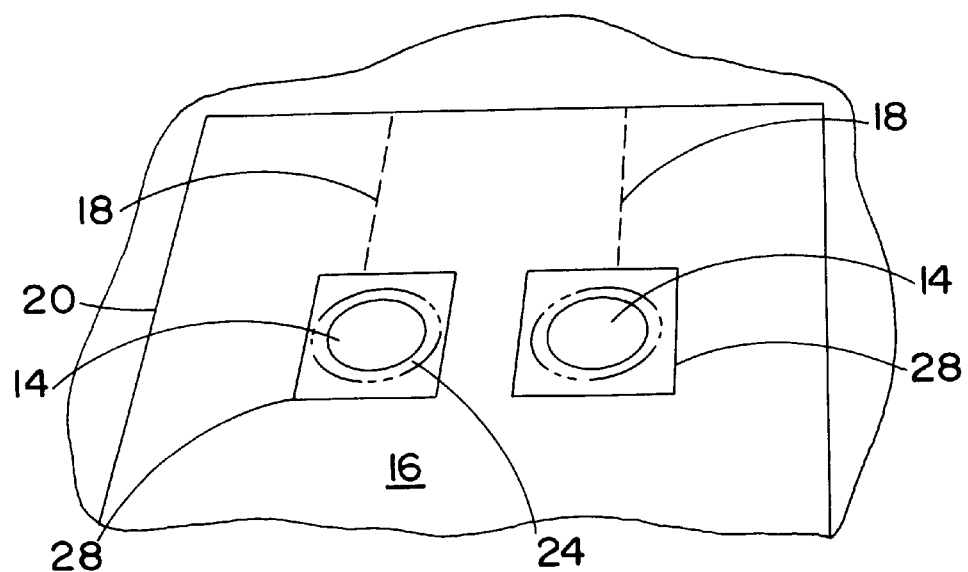
FIG. 2 is view of a portion of the surgical drape of FIG. 1 showing the perforated absorbent pad portion of that embodiment.

Repeat use of reference characters in the present specification and drawings is intended to represent the same or analogous features or elements of the invention.

DETAILED DESCRIPTION OF PREFERRED EMBODIMENT

It is to be understood by one of ordinary skill in the art that the present discussion is a description of exemplary embodiments only, and is not intended as limiting the broader aspects of the present invention, which broader aspects are embodied in the exemplary construction.

Referring now to FIG. 1, the surgical drape 10 of the present invention is illustrated. Surgical drape 10 includes a base sheet 12 having an upper surface 13 which will not be in contact with the patient and a bottom surface 15 (shown in FIG. 6) which will be in contact with the patient. Although it may have varying dimensions and shapes, drape 10 is normally rectangular and sized to cover at least a majority of a patient's body during a surgical procedure.

Surgical drape 10 includes one or more apertures, or fenestrations, 14 that provide the surgeon with access to an operative site on a patient. As better shown in FIG. 6, the patient's body may be accessed during surgery through fenestrations 14. The particular embodiment shown in FIG. 1 has two fenestrations 14. However, as explained herein, the present invention is also directed to surgical drapes having only one such opening.

Drape 10 is comprised of two sheet materials—a base sheet 12 and a reinforcing pad 20 superimposed on and preferably affixed in some manner to the upper surface 13 of base sheet 12. Reinforcing pad 20 is preferably constructed of a material which has an absorbent upper surface 16 to absorb fluids near the operative site. The reinforcement pad 20 also provides greater resistance to penetration of instruments placed on top of the drape during surgery.

Figure 3:
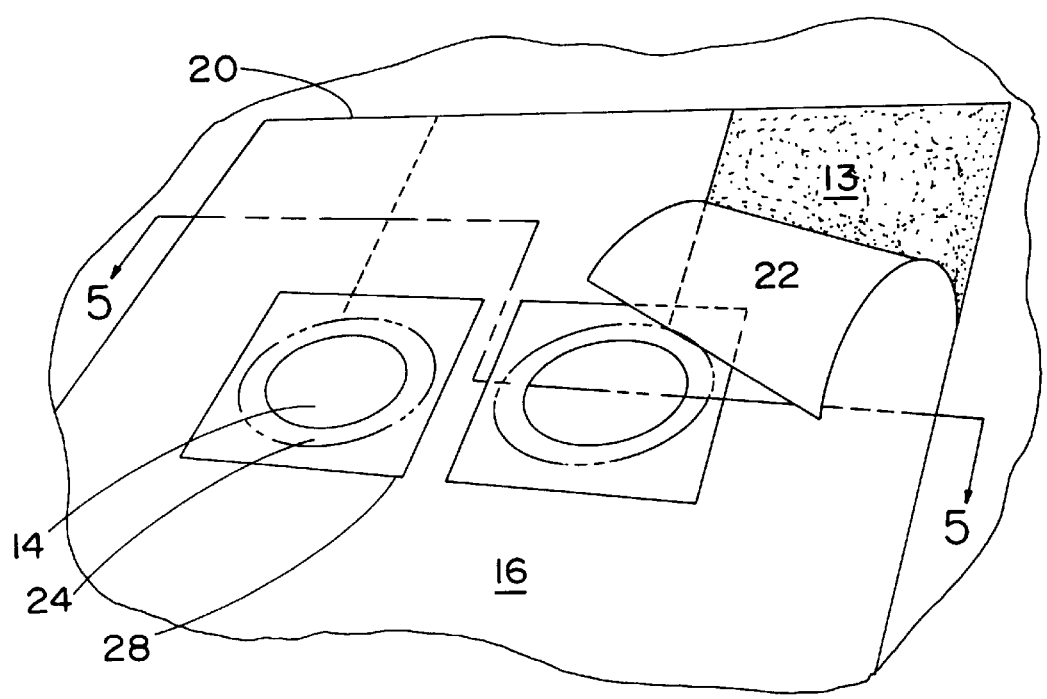
FIG. 3 is a view of a portion of the surgical drape of FIG. 1 with the absorbent pad portion being pulled away from the underlying base sheet.

Reinforcing pad 20 is normally made from a fluid-absorbing material backed by a fluid-repellant or fluid-impervious film layer 22 (shown in FIG. 3). The film layer side of the pad 20 is secured to upper surface 13 of base sheet 12 by an adhesive. The fluid-absorbing absorbent upper surface 16 of pad 20 remains exposed and available to absorb fluids emitted from the surgical wound.

Figure 5:
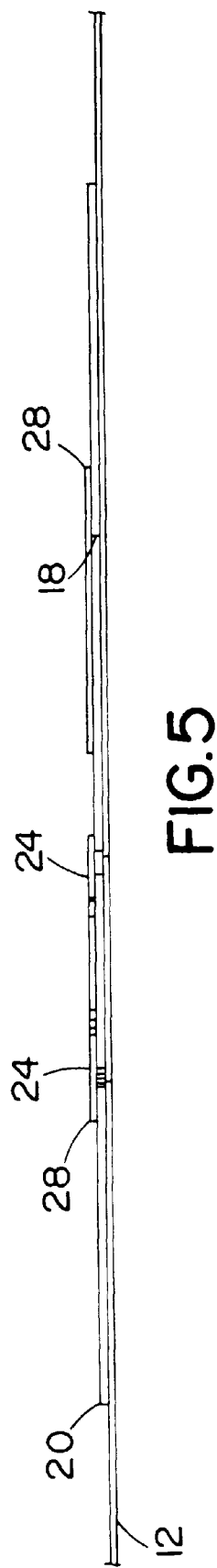
FIG. 5 is a side elevation view of the surgical drape of FIG. 3 along the cutaway line 5—5.
Figure 5A:
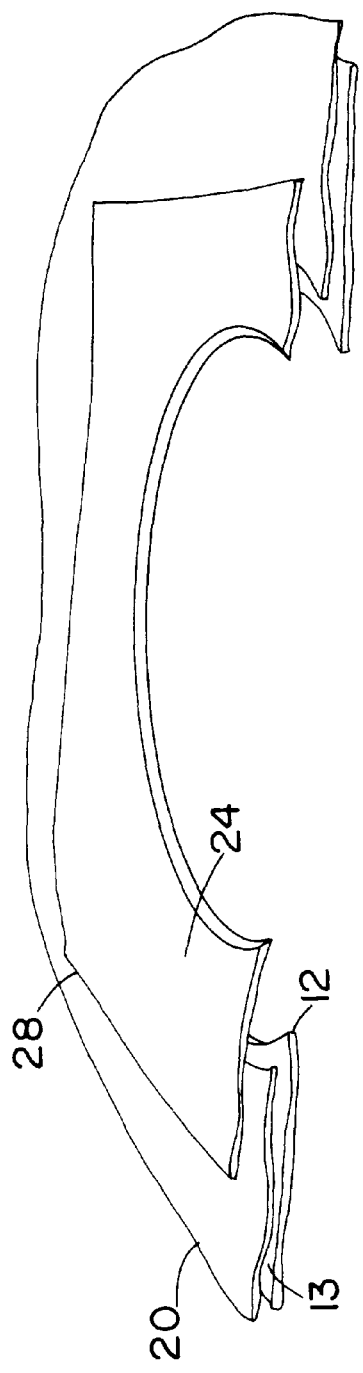
FIG. 5A is an exploded plan view of a portion of a cutaway portion of the surgical drape of FIG. 1.

Reinforcement pad 20 includes openings similar in size to openings in base sheet 12 which, in combination, form fenestrations 14. Although the fenestrations shown in the Figures are circular, it is to be understood that the shape and size of the openings, as well as the number and location of the openings on the drape, will depend on the particular surgical procedure involved. The form and placement of the dual fenestrations 14 in the exemplary Figures are for a femoral angiography procedure. As shown in FIG. 5, the edges of base sheet 12 and reinforcement pad 20 that define fenestration 14 do not meet exactly when surgical drape 10 is formed. Obviously, this is matter of design preference and the openings in base sheet 12 and pad 20 may be of the same size.

Preferably, surgical drape 10 includes an adhesive bearing plastic material 28 that circumscribes and extends into the apertures of base sheet 12 and pad 20. The adhesive carried on the surface of the plastic material 28 which will be next to the patient's body allows fenestration 14 to be secured around the operative site. The tacky and pressure-sensitive adhesives used may be of any biologically acceptable adhesive. Examples of such adhesive materials are described in U.S. Pat. No. 3,669,106 entitled "Surgical Drape with Adhesive Attachment Means" to Schrading et. al, which is incorporated herein in its entirety by reference. The adhesive carried on plastic material 28 serves two functions—it adheres the plastic material to the absorbent pad's upper surface 16 and adheres drape 10 to the patient's body when the drape is in use to provide a seal around the surgical incision site.

Figure 4:
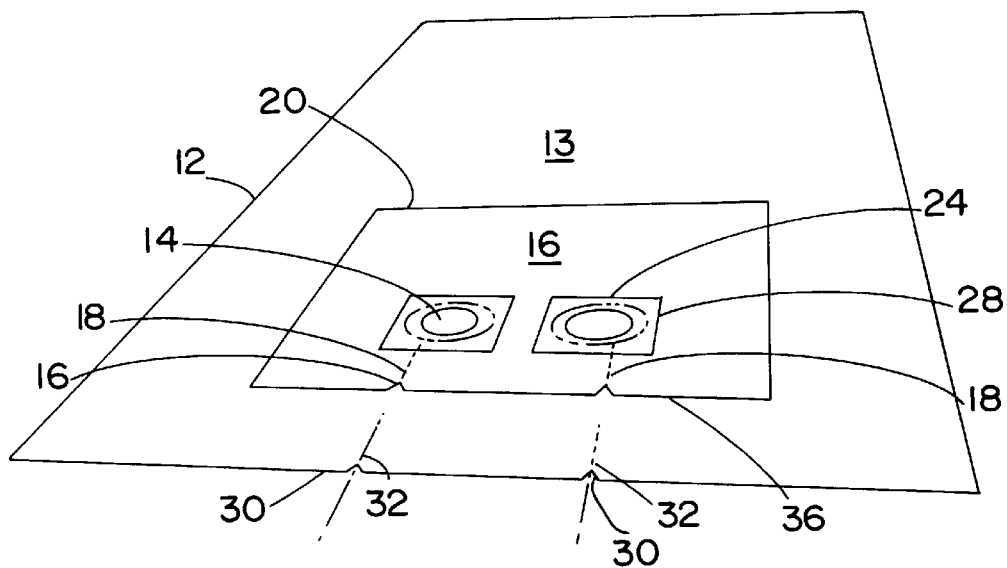
FIG. 4 is a view of a surgical drape in accordance with a further embodiment of the present invention.

Referring to FIGS. 3–5, adhesive bearing plastic material 28, in the embodiment illustrated, is a sheet of plastic having an aperture therein and a pressure-sensitive adhesive carried on one side that is to contact the absorbent pad's upper surface 16. The adhesive bearing plastic material 28 may be made of any shape, provided it has sufficient surface area to allow attachment to the absorbent pad's upper surface 16 and has an extending edge 24 that extends across the periphery of the apertures of base sheet 12 and pad 20. The surface of extending edge 24 which carries the adhesive allows surgical drape 10 to be adhered in a relatively tight manner to the patient's body at the operative site.

To prevent the adhesive surface of extending edge 24 from sticking to itself or other portions of drape 10 prior to use, a sheet of conventional removable release material (not shown), such as wax- or silicone-coated paper, may be placed on the bottom surface 15 of base sheet 12 until the drape is ready for use. In use, the releasable cover sheet is removed and the drape is unfolded over the patient so that the portion of the extending edge 24 of adhesive bearing plastic material 28 is presented toward the patient's body.

Once unfolded, the extending edge 24 is pressed onto the patient's skin to create a closed area around the surgical incision site. The release paper may have positioning directions written on the surface opposite the adhesive side of the plastic material 28. Such directions would normally indicate how the drape is to be placed on the patient. For example, the release paper may have the word "Head" with an arrow indicating that the drape is to be placed in the arrow direction toward the patient's head.

The combination of base sheet 12 and the absorbent reinforcement pad 20 result in a tear-away surgical drape. As discussed herein, base sheet 12 is made of a material that is relatively easy to tear, but the absorbent reinforcement pad 20 is made of a material that is harder to tear. This is due, in part, to the presence of impervious film layer 22. In fact, such reinforcing pads have usually needed to be cut with scissors. The use of scissors this close to the operative site obviously puts them in a position where they could cut the patients, an inserted tube, or the like.

The reinforcing pad 20 of the present invention is made easy to tear by providing perforations 18 therethrough. The perforations form a score line along which the reinforcing pad 20 may be easily separated. The perforations penetrate through the entire thickness of reinforcing pad 20. The sterile field, however, is maintained because base sheet 12 is not perforated.

The perforations forming the score line in the accompanying Figures are shown as beginning at an edge of reinforcing pad 20 and continuing until the edge of the pad defining fenestration 14 is reached. However, it is possible to achieve the benefits of the present invention even if the perforations do not begin exactly at the outside edge of pad 20. In addition, the extending edge 24 of adhesive bearing plastic material 28 may, itself, have perforations which would continue the score line past the edge of pad 20 defining fenestration 14. The perforations may be aligned in any direction, provided they run to the edge or almost to the edge of pad 20 where fenestration 14 is defined and provided they allow one to easily tear pad 20 beginning near an outer edge. Any of such constructions fall within the broad scope of the present invention.

Either one or both of base sheet 12 and pad 20 may have one or more notches at their edges which correspond in relative linear alignment to the perforation score line 18 on pad 20. As seen in FIG. 4, notch or notches 30 may be provided at an outer edge of base sheet 12. The notches are in general alignment with score line 18.

Although base sheet 12 should not have perforations which extend all the way to the edge of pad 20, several additional perforations 32 may be located, with or without notches 30, at the very outer edge of base sheet 12 in order to ease the initial tearing of base sheet 12. Because such perforations would be located a substantial distance from the surgical site, the desired sterile field would still be maintained. In addition, reinforcing pad 20 may have notches such as those shown at reference numeral 36 to further enhance the tearability of pad 20.

Figure 6:
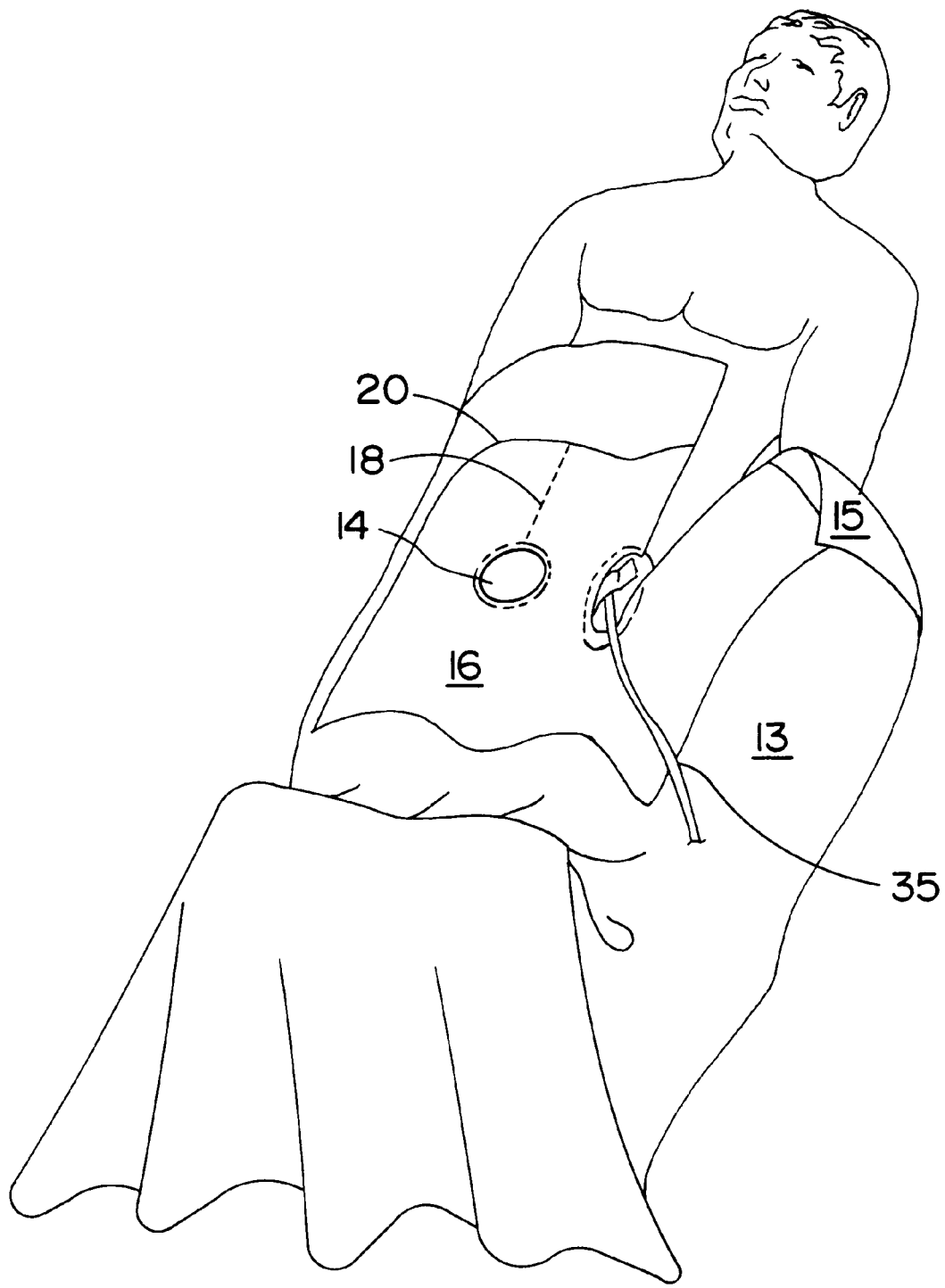
FIG. 6 is a plan view of the surgical drape of FIG. 1 being torn away from a patient after completion of a surgical procedure.

As shown in FIG. 6, after the surgical procedure is completed, the drape may be torn away without disturbing any apparatus, such as tube 35, that still remains connected to the patient at the surgical site. One merely begins tearing base sheet 12 at a point on the outer edge thereof which corresponds to the general linear alignment of score line(s) 18. If a notch 30 as shown in FIG. 4 is provided, tearing would begin at that point. One continues tearing base sheet 12 until the perforation score line 18 on pad 20 is reached, and continues tearing both base sheet 12 and pad 20 until the tear goes to and through extending edge 24 on adhesive bearing plastic material 28. The base sheet 12 and pad 20 are then pulled back away from the patient and the drape may then be completely removed and disposed of without touching the remaining apparatus.

Scissors may be used to begin the cutting of base sheet 12. Their use at a point sufficiently far away from the patient would not increase the risk associated with drape removal as it would if scissors or other cutting instrument were used to cut all the way through to the fenestration.

Alternatively, pad 20 may be torn away and removed first before removing underlying base sheet 12 from the patient. Instead of tearing base sheet 12, pad 20 could be grabbed, pulled away from pad 20, and pulled apart along perforation score line 18. Base sheet 12 would then be torn off the patient as described above.

Removal of pad 20 without tearing base sheet 12 could also be useful where pad 20 has become highly soiled with blood and other fluids and its removal before the end of the surgery is necessary. If a second pad is needed to replace the first pad, the presence of score line 18 would allow a new, clean pad 20 to be torn and then fitted around the surgical site, with or without the application of additional adhesive on film layer 22. Although this new pad would be pre-torn (if the surgical apparatus remains in place through the openings in base sheet 12), base sheet 12 would still be in place to maintain the sterile field.

Other features may be added to the present invention and still fall within its scope. For example, various instrument holding compartments such as that shown in U.S. Pat. No. 5,074,316 to Dowdy as well as non-skid instrument pads such as that described in U.S. Pat. No. 3,856,006 to Krzewinski may be utilized.

Drape 10 may be disposable or reusable. Preferably, it is disposable. If disposable, one drape that may be used for this purpose is described in U.S. Pat. No. 3,902,484 entitled "Disposable Surgical Drape" to Winters, which is incorporated herein in its entirety. As described therein, the upper surface 13 of base sheet 12 of the present invention would have the fluid impervious layer or film 22 carried on the backside of pad 20 bonded thereto. This bonding could be by any suitable means such as by an adhesive. Film layer 22 provides a fluid impervious barrier in the primary operative area so that any fluids contacting this area cannot strike through the pad. The absorbency of the remainder of pad 20 prevents excessive fluid run-off while the liquid impervious film layer 22 prevents passage of the fluid to the base sheet 12. In certain embodiments, a pad with a relatively high coefficient of friction on the upper surface may provide a substantially non-slip surface which lessens the chance of accidental falling of surgical instruments and the like placed on the absorbent upper surface 16 of pad 20 during surgery.

The nonwoven fabric from which such base sheets are normally made should be relatively soft and have good draping and folding characteristics. Additionally, the nonwoven fabric should be capable of being subjected to a sterilization treatment without being adversely affected. The use of nonwoven fabrics for disposable drapes eliminates the laundering, resterilization, and handling costs associated with linen drapes.

The selection of a nonwoven fabric having the above-mentioned qualities is within the skill of those working in this art. Materials such as those used in the manufacture of single-use surgical drapes which are usually treated with a water-repellent finish and which may even be treated with a fire-retardant composition, are applicable to the present invention.

Examples of suitable disposable liquid repellent drapable fabrics for making the base sheet include meltblown, spunbond nonwoven fabrics sold by Kimberly-Clark Corporation under the trademark EVOLUTION FABRIC®, described, for example, in U.S. Pat. No. 4,041,203 entitled "Nonwoven Thermoplastic Fabric" to Brock et al. and scrim-reinforced tissue products described for example in U.S. Pat. No. 3,072,511 entitled "Laminated Sheet Material" to Harwood. Other examples of nonwoven fabrics are described in U.S. Pat. Nos. 3,484,330 entitled "Disposable Fabric" to Sokolowski et. al., 5,482,765 entitled "Nonwoven Fabric Laminate with Enhanced Barrier Properties" to Bradley et al., and 5,151,321 entitled "Method of Making Conductive, Water and/or Alcohol Repellent Nonwoven Fabric and Resulting Product" to Reeves et al. The entirety of all five of these patents is incorporated herein by reference.

As for the reinforcing absorbent pad 20, various materials may also be used. The smaller reinforcing pad 20 may be a foam/film laminate of the type described in U.S. Pat. Nos. 3,699,106 entitled "Surgical Drape with Adhesive Attachment Means" to Schrading and 3,668,050 entitled "Surgical Drape" to Donnelly. One particularly acceptable pad for this use is described in U.S. Pat. No. 5,540,979 entitled "Porous Non-Woven Bovine Blood-Oxalate Absorbent Structure" to Yahiaoui et al. The entirety of all three of these patents is incorporated herein by reference. Another acceptable pad is made of a spun bond, meltblown material sold under the name CONTROL PLUS® by Kimberly-Clark Corporation.

The film layer 22 of pad 20 may be anti-static polyethylene, polypropylene, polyethylene methyl acrylate copolymer, or vinyl chloride films. The film provides the described fluid impervious barrier on top of the operative area of base sheet 12 so that any liquid contacting the pad 20 will not strike through to the base sheet 12. The fluid absorbent material may be bonded to the film layer 22 by any suitable means such as adhesive bonding, fusing or by extruding the film directly. Examples of suitable absorbent materials include polyester and polyether polyurethane foams, with thicknesses anywhere in the range of from about 25 mils to about 100 mils.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A tear-away surgical drape for covering the body of a patient during surgery, said drape comprising:

a) a base sheet having an upper surface and a bottom surface and at least one edge, said base sheet defining at least one aperture therein for surrounding a surgical site on the body of said patient, and said base sheet being constructed of a tear-away material; and b) a reinforcing pad attached to the upper surface of said base sheet, said pad defining at least one aperture therein for surrounding a surgical site on the body of said patient and being positioned on said base sheet so that said aperture on said base sheet and said aperture on said pad are in substantial alignment to define a fenestration in said drape, said pad having an upper surface with fluid absorbent capabilities, said pad further having a plastic material with an adhesive material on one surface thereof, said plastic material being positioned and located on said pad so that said plastic material extends across said aperture defined by said pad and so that the adhesive surface of said plastic material may be adhered to the patient's body when the drape is in position during surgery, and said pad further having perforations extending therethrough and away from said aperture toward an edge of said base sheet to define a score line along which said pad may be torn when said drape is torn away from a patient.

2. The tear-away surgical drape of claim 1 wherein said score line extends from said aperture all the way to an end of said pad.

3. The tear-away surgical drape of claim 1 wherein said base sheet has a notch at an edge thereof which is in substantial linear alignment with said score line on said pad.

4. The tear-away surgical drape of claim 1 wherein said base sheet has perforations which are in substantial linear alignment with said score line on said pad.

5. The tear-away surgical drape of claim 1 wherein both of said base sheet and said reinforcing pad have at least two apertures therethrough which are in substantial alignment when said pad is attached thereto.

6. The tear-away surgical drape of claim 1 wherein said pad is attached to said upper surface of said base sheet by an adhesive material.

7. The tear-away surgical drape of claim 1 wherein said pad has a notch at an edge thereof which is in substantial linear alignment with said score line.

8. A tear-away surgical drape for covering the body of a patient during surgery, said drape comprising a tearable base sheet having an upper surface with a pad adhered thereto and a bottom surface for contact with said patient, said base sheet and said pad defining an aperture therein through which an operation on the patient's body may be performed when said drape is in place on said patient, said drape having an adhesive material on said bottom surface thereof for adhering said drape in position during surgery, said pad having perforations therein defining a score line extending from said aperture to an end of said pad to allow said pad to be easily torn away from said patient after surgery when said base sheet is torn away.

9. The tear-away surgical drape of claim 8 wherein said base sheet has a notch at an end thereof which is located in substantial linear alignment with said score line on said pad.

10. The tear-away surgical drape of claim 8 wherein said score line extends from said aperture all the way to an end of said pad.

11. A tear-away surgical drape for covering the body of a patient during surgery, said drape comprising:

a) a base sheet having an upper surface and a bottom surface and four edges, said base sheet defining at least one aperture therein for surrounding a surgical site on the body of said patient, and said base sheet being constructed of a tear-away material;

b) a reinforcing pad attached to the upper surface of said base sheet, said pad defining at least one aperture therein for surrounding a surgical site on the body of said patient and being positioned on said base sheet so that said aperture on said base sheet and said aperture on said pad are in substantial alignment to define a fenestration in said drape, said pad having an upper surface with fluid absorbent capabilities, said pad further having a plastic material with an adhesive material on one surface thereof, said plastic material being positioned and located on said pad so that said plastic material extends across said aperture defined by said pad and so that the adhesive surface of said plastic material may be adhered to the patient's body when the drape is in position during surgery, and said pad further having perforations extending therethrough and away from said aperture towards an edge of said base sheet and to an end of said pad to define a score line along which said pad may be torn when said drape is torn away from a patient; and c) said base sheet having a notch located at an edge thereof and positioned in substantial linear alignment with said score line on said pad.

\* \* \* \* \*